(12) United States Patent
Bae et al.

(10) Patent No.: US 8,591,424 B2
(45) Date of Patent: Nov. 26, 2013

(54) PRESSURIZING MODULE AND BLOOD PRESSURE MEASURING DEVICE INCLUDING THE SAME

(75) Inventors: Sang-kon Bae, Seongnam (KR); Kun-soo Shin, Seongnam (KR); Jong-pal Kim, Seoul (KR); Youn-ho Kim, Hwaseong (KR)

(73) Assignee: Samsung Electronics Co., Ltd. (KR)

( * ) Notice: Subject to any disclaimer, the term of this patent is extended or adjusted under 35 U.S.C. 154(b) by 359 days.

(21) Appl. No.: 12/560,910

(22) Filed: Sep. 16, 2009

(65) Prior Publication Data

US 2010/0121206 A1    May 13, 2010

(30) Foreign Application Priority Data

Nov. 12, 2008  (KR) .................. 10-2008-0112220

(51) Int. Cl.
*A61B 5/022* (2006.01)

(52) U.S. Cl.
USPC ............ 600/499; 600/493; 600/490; 600/485

(58) Field of Classification Search
USPC ........................... 600/485, 490–499; 137/225
See application file for complete search history.

(56) References Cited

U.S. PATENT DOCUMENTS

| | | | | |
|---|---|---|---|---|
| 4,784,152 A | * | 11/1988 | Shinoda et al. | 600/503 |
| 4,966,156 A | * | 10/1990 | Perry et al. | 600/485 |
| 5,031,631 A | * | 7/1991 | Kawamura et al. | 600/498 |
| 5,179,956 A | * | 1/1993 | Harada et al. | 600/485 |
| 5,649,542 A | * | 7/1997 | Archibald et al. | 600/485 |
| 6,251,080 B1 | * | 6/2001 | Henkin et al. | 600/490 |
| 6,290,650 B1 | * | 9/2001 | Butterfield et al. | 600/485 |
| 6,939,306 B2 | * | 9/2005 | Tseng | 600/494 |
| 7,503,896 B2 | * | 3/2009 | Miele et al. | 600/454 |
| 2003/0149369 A1 | * | 8/2003 | Gallant et al. | 600/485 |
| 2004/0210143 A1 | * | 10/2004 | Gallant et al. | 600/485 |
| 2005/0049512 A1 | * | 3/2005 | Tseng | 600/490 |
| 2006/0184051 A1 | * | 8/2006 | Hempstead et al. | 600/485 |
| 2008/0161637 A1 | * | 7/2008 | Sun et al. | 600/16 |
| 2008/0177187 A1 | * | 7/2008 | Lee et al. | 600/490 |

FOREIGN PATENT DOCUMENTS

| | | |
|---|---|---|
| JP | 63-267336 | 11/1988 |
| JP | 02-001226 | 1/1990 |
| JP | 07-124128 | 5/1995 |
| KR | 1019990036662 A | 5/1999 |
| KR | 1020060053936 A | 5/2006 |
| KR | 1020060118386 A | 11/2006 |
| WO | WO 2006043785 A1 * | 4/2006 |

OTHER PUBLICATIONS

"Shaft." Oxford English Dictionary. 19 pages.*

* cited by examiner

*Primary Examiner* — Navin Natnithithadha
*Assistant Examiner* — Meredith Weare
(74) *Attorney, Agent, or Firm* — Cantor Colburn LLP

(57) ABSTRACT

Provided are a pressurizing module and a blood pressure measuring device including the pressurizing module. The pressurizing module includes a driving block optionally discharging compressed air; and a bellows-type airbag formed to overlap with the driving block, and comprising an inner space accommodating the compressed air discharged from the driving block, a plurality of wrinkles flattened so as to expand the inner space, and a pressurizing surface formed at an end portion of the wrinkles and spaced apart from the driving block as the inner space expands.

10 Claims, 3 Drawing Sheets

PRESSURIZING MODULE AND BLOOD PRESSURE MEASURING DEVICE INCLUDING THE SAME

CROSS-REFERENCE TO RELATED APPLICATIONS

This application claims priority to Korean Patent Application No. 10-2008-0112220, filed on Nov. 12, 2008, and all benefits therefrom under 35 U.S.C. §119, the contents of which in its entirety are herein incorporated by reference.

BACKGROUND

1. Field

Disclosed herein is a blood pressure measuring device for measuring a blood pressure of a patient either once or continuously.

2. Description of the Related Art

Various types of blood pressure measuring devices have been developed in the interests of monitoring the blood pressure of individuals and thereby improving the public health. Blood pressure measuring methods include a Korotkoff sounds method, an oscillometric method, a tonometric method, and the like. The Korotkoff sounds method, which is a typical blood pressure measuring method, measures the systolic pressure at which the pulse sound is first heard and the diastolic pressure at which the pulse sound is barely audible in a depressurization process after blood flow is blocked by sufficiently pressurizing a body part through which arterial blood flows.

The oscillometric method and the tonometric method are used in digital blood pressure measuring devices. The oscillometric method measures the systolic pressure and the diastolic pressure by detecting a pulse wave generated in a depressurization process that depressurizes a body part at a constant speed. The detection of the pulse wave is conducted after sufficiently pressurizing the body part through which arterial blood flows so as to block arterial blood flow. This is similar to the Korotkoff sounds method. The oscillometric method may also be conducted in a pressurization process that pressurizes the body part at a constant speed. A pressure at which the amplitude of a pulse waveform is at a specific level may be measured as a function of the systolic pressure or the diastolic pressure, as compared to a pressure at which the amplitude of the pulse waveform is at a maximum. Alternatively, a pressure at which the amplitude of the pulse waveform varies greatly may be measured as a function of the systolic pressure or the diastolic pressure. During the depressurization process of the body part at a constant speed after the pressurization process, the systolic pressure is measured before the moment at which the amplitude of the pulse waveform is at the maximum, and the diastolic pressure is measured after the moment at which the amplitude of the pulse waveform is at the maximum. On the contrary, in the pressurization process of the body part at a constant speed, the systolic pressure is measured after the moment at which the amplitude of the pulse waveform is at the maximum, and the diastolic pressure is measured before the moment at which the amplitude of the pulse waveform is at the maximum.

The tonometric method compresses a body part so that arterial blood flow is not completely blocked and continuously measures blood pressure by using the size and form of a sphygmus wave generated by pressurizing the body part.

Recently, a portable blood pressure measuring device, which can measure blood pressure by using an oscillometric method or a tonometric method without any inconvenience to a user has been developed. The portable blood pressure measuring device can be installed in a body part such as a wrist. However, the portable blood pressure measuring device needs improvement in terms of size and precision control of blood vessel pressurization pressure.

SUMMARY

One or more embodiments include a pressurizing module, which is reduced in size and has increased precision control of blood vessel pressurization pressure, and a blood pressure measuring device including the pressurizing module.

Additional aspects and/or advantages will be set forth in part in the description which follows and, in part, will be apparent from the description, or may be learned by practice of the invention.

To achieve the above and/or other aspects and advantages, one or more embodiments may include a pressurizing module including a driving block optionally discharging compressed air; and a bellows-type airbag formed to overlap the driving block; the bellows-type airbag comprising an inner space accommodating the compressed air discharged from the driving block, a plurality of wrinkles flattened so as to expand the inner space, and a pressurizing surface formed at an end portion of the wrinkles and spaced apart from the driving block as the inner space expands.

The driving block may include a motor having a rotation axis, a cam for converting rotary motion of the rotation axis into a reciprocating motion in a direction perpendicular to an extension direction of the rotation axis, a cylinder having a piston which is connected to the cam and reciprocates, an injecting path formed so that the compressed air generated by the reciprocating motion of the piston moves toward the bellows-type airbag, and a countercurrent preventing valve for preventing a countercurrent of air from flowing along the injecting path to the cylinder.

The driving block may further include a discharging path that branches off the injecting path, and a decompression valve formed at an end portion of the discharging path and optionally inducing the compressed air to flow along the discharging path.

The driving block may further include a deceleration unit for reducing a rotation speed of the rotation axis and transferring the rotation speed to the cam.

The deceleration unit may include a first gear disposed on the rotation axis and rotating at the same speed as the rotation axis, and a second gear engaged with the first gear and having a diameter greater than that of the first gear.

The pressurizing module may further include a coupling block having a connection path, is the coupling block being interposed between the driving block and the bellows-type airbag and induces the compressed air discharged from the driving block to flow into the inner space of the bellows-type airbag.

The coupling block may include a hole allowing airflow between the connection path and the inner space of the bellows-type airbag, and the hole may be disposed in a manner so as not to overlap the wrinkles.

The coupling block may further include a buffer chamber inside the coupling block in order to suppress a fast inflow of air into the inner space of the bellows-type airbag.

To achieve the above and/or other aspects and advantages, one or more embodiments may include blood pressure measuring device for pressurizing a blood vessel of a patient, the blood pressure measuring device including the pressurizing module, a pressure sensor attached to a pressurizing surface of the bellows-type airbag and detecting a sphygmus wave and pressure of a blood vessel from the blood vessel, and a blood pressure calculation processor for calculating blood pressure of the patient on the basis of the sphygmus wave and the pressure of the blood vessel detected in the pressure sensor.

The blood vessel may be a radial artery inside a patient's wrist.

The blood pressure measuring device may further include a wrist band surrounding the patient's wrist so as to attach the blood pressure measuring device to the patient's wrist.

BRIEF DESCRIPTION OF THE DRAWINGS

The above and other aspects, advantages, and features will become more apparent and by describing in further detail exemplary embodiments thereof with reference to the attached drawings, in which.

DETAILED DESCRIPTION

Figure 1:
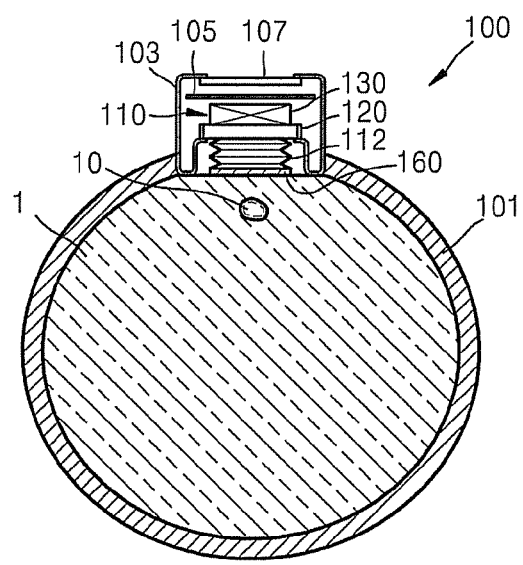
FIG. 1 is an exemplary schematic vertical cross-sectional view of a blood pressure measuring device.

Reference will now be made in detail to embodiments, examples of which are illustrated in the accompanying drawings, wherein like reference numerals refer to the like elements throughout. In this regard, the present invention may be embodied in many different forms and should not be construed as being limited to the embodiments set forth herein. Accordingly, embodiments are merely described below, by referring to the figures, to explain aspects of the present invention.

Aspects, advantages, and features of exemplary embodiments of the invention and methods of accomplishing the same may be understood more readily by reference to the following detailed description of embodiments and the accompanying drawings. The exemplary embodiments of the invention may, however, may be embodied in many different forms, and should not be construed as being limited to the embodiments set forth herein. Rather, these embodiments are provided so that this disclosure will be thorough and complete and will fully convey the concept of the invention to those skilled in the art, and the exemplary embodiments of the invention will only be defined by the appended claims. Like reference numerals refer to like elements throughout the specification.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

It will be understood that, although the terms first, second, third, etc., can be used herein to describe various elements, components, regions, layers and/or sections, these elements, components, regions, layers and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the exemplary embodiments of the invention.

Spatially relative terms, such as "below," "lower," "upper" and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device can be otherwise oriented (rotated 90 degrees or at other orientations) and the spatially relative descriptors used herein interpreted accordingly.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation can result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

FIG. 1 is an exemplary schematic vertical cross-sectional view of a blood pressure measuring device 100.

Referring to FIG. 1, the blood pressure measuring device 100 is designed for a wrist 1 through which a radial artery 10 passes, so as to facilitate detecting a sphygmus wave and pressure of a blood vessel (e.g., the radial artery 10). The blood pressure measuring device 100 includes a wrist band 101 surrounding the wrist 1 of a patient, a pressurizing module 110 for pressurizing a radial artery 10 formed inside the wrist 1, which is the point where blood pressure is to be measured. A pressure sensor 160 is attached to an end portion of the pressurizing module 110 and contacts the patient's skin that is adjacent to the radial artery 10 to detect a sphygmus wave and pressure of the blood vessel. The detection of the sphygmus wave and pressure of the blood vessel is conducted to determine the blood pressure of the patient. A blood pressure calculation processor for calculating the patient's blood pressure on the basis of the sphygmus wave and the pressure in the blood vessel are contained in the pressure sensor 160. The pressurizing module 110 is formed inside a housing 103 connected to the wrist band 101. The blood pressure calculation processor is realized by an electrical circuit formed in a circuit board 105 disposed inside the housing 103. The blood pressure measuring device 100 further includes a display panel 107 capable of visually showing results of the blood pressure measurement.

The pressurizing module 110 includes a driving block 130 for optionally discharging compressed air, a bellows-type airbag 112 disposed in the housing 103 to overlap the driving block 130 and accommodating the compressed air discharged from the driving block 130, and a coupling block 120 interposed between the driving block 130 and the bellows-type airbag 112. The pressure sensor 160 is attached to a pressurizing surface 115 (see FIG. 5A) of the bellows-type airbag 112.

Figure 2:
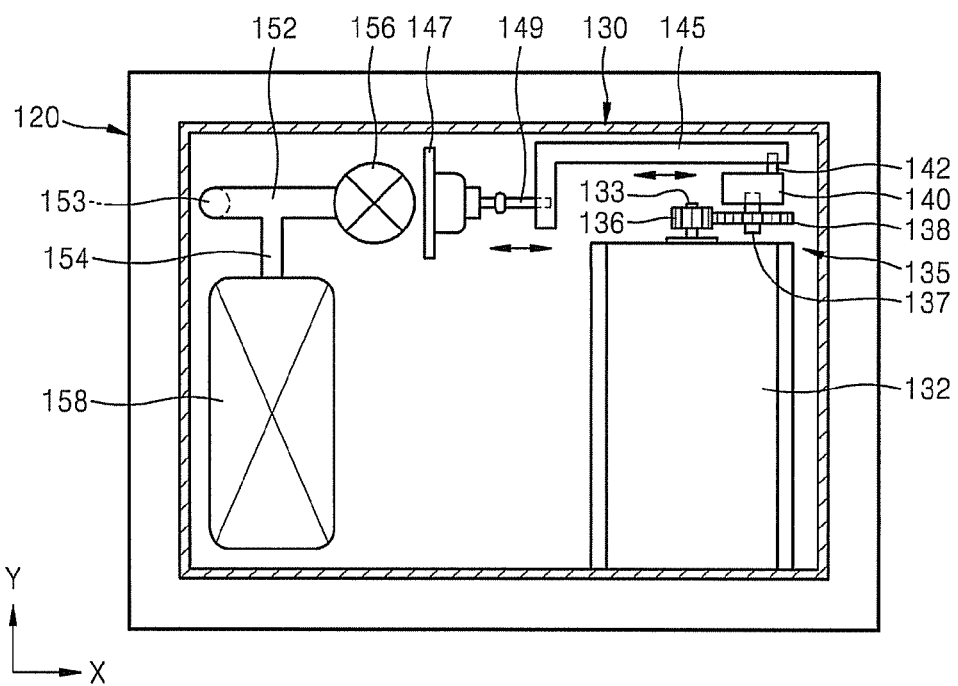
FIG. 2 is a schematic plane view illustrating the inside of a driving block of FIG. 1.
Figure 3:
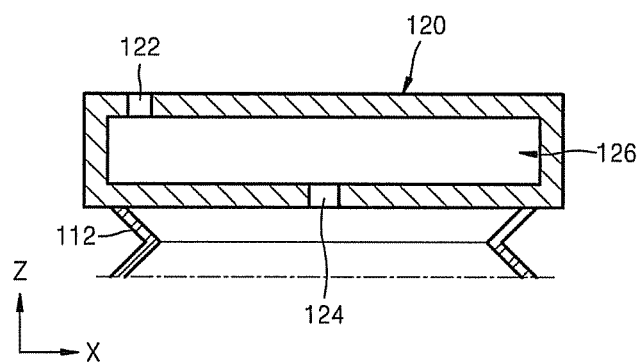
FIG. 3 is a cross-sectional view of a coupling block of FIG. 1.
Figure 4:
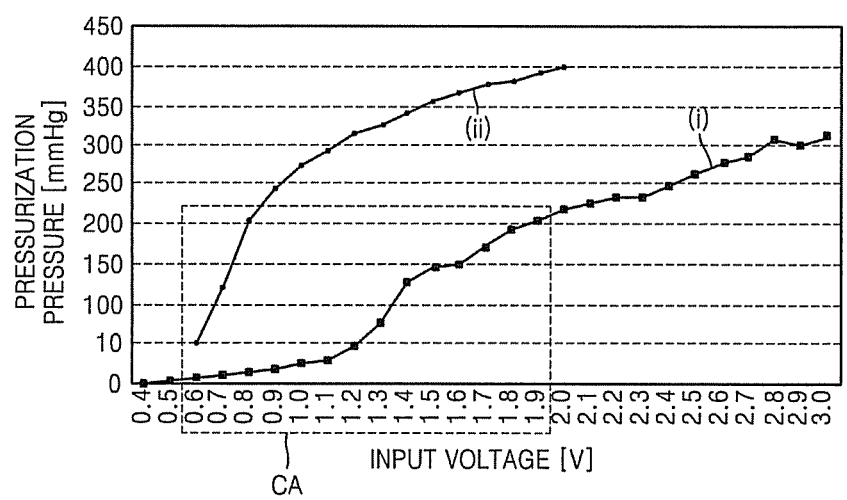
FIG. 4 is a graph illustrating a relation between a motor input voltage and pressurization pressure in a pressurizing module when compared with a conventional pressurizing module.
Figure 5A:
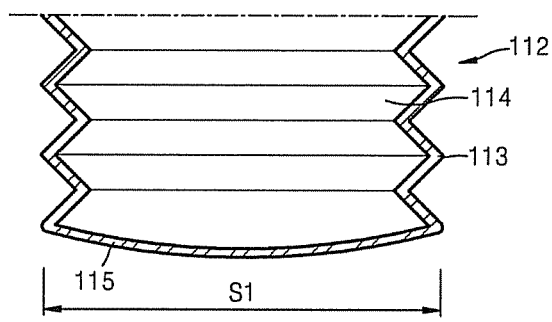
FIG. 5A is an exemplary cross-sectional view illustrating a case where a bellows-type airbag of FIG. 1 is expanded.
Figure 5B:
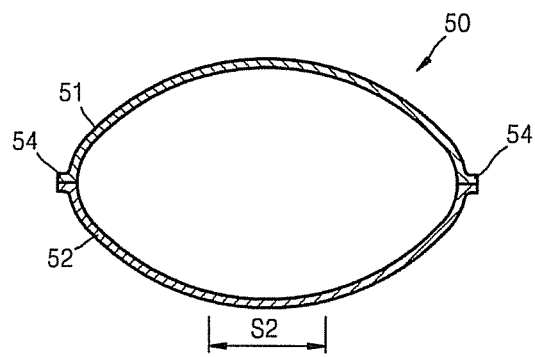
FIG. 5B is a cross-sectional view illustrating a case where a pouch-type airbag is expanded.

FIG. 2 is an exemplary schematic plane view illustrating the inside of a driving block of FIG. 1. FIG. 3 is an exemplary cross-sectional view of a coupling block of FIG. 1. FIG. 4 is a graph illustrating a relation between a motor input voltage and a pressurization pressure in a pressurizing module according to an embodiment of the present invention and in a conventional pressurizing module. FIG. 5A is an exemplary cross-sectional view illustrating a case where a bellows-type airbag of FIG. 1 is expanded, and FIG. 5B is an exemplary cross-sectional view illustrating a case where a pouch-type airbag is expanded.

Referring to FIG. 5A, the bellows-type airbag 112 includes an inner space 114 accommodating the compressed air discharged from the driving block 130, a plurality of wrinkles 113 for forming the inner space 114, and the pressurizing surface 115. When air is injected into the inner space 114, the wrinkles 113 are straightened (i.e., they are expanded) and the volume of the inner space 114 expands and when air is ejected from the inner space 114, the wrinkles 113 reform and the volume of the inner space 114 is reduced. The pressurizing surface 115 moves in a direction away from the driving block 130 (see FIG. 1) and the coupling block 120 as the volume of the inner space 114 expands. That is, if air is injected into the inner space 114 when the patient is wearing the blood pressure measuring device 100, the pressurizing surface 115 pressurizes the wrist 1 (see FIG. 1) and the radial artery 10 (see FIG. 1) inside the wrist 1.

Referring to FIG. 2, the driving block 130 includes a motor 132 including a rotation shaft 133 inside the motor 132, a cam 145 converting rotary motion of the rotation shaft 133 into a reciprocating motion in an X-axis direction perpendicular to a Y-axis direction; the Y-direction being an extension direction of the rotation shaft 133. A deceleration unit 135 decelerates the rotation speed of the rotation shaft 133 to transfer the rotation to the cam 145, and a cylinder 147 including a piston 149, which is connected to the cam 145 and reciprocates. The motor 132 may control the rotation speed of the rotation shaft 133 by controlling the size of an input voltage.

The deceleration unit 135 includes a first gear 136 and a second gear 138, which is engaged with the first gear 136. The first gear 136 is fixedly disposed on the rotation shaft 133 and rotates at the same speed as the shaft 133. In one embodiment, the first gear 136 is in mechanical communication with the rotation shaft 133 and rotates at the same speed as the shaft 133. The second gear 138 has a diameter greater than that of the first gear 136. Referring to FIG. 2, a diameter ratio of the first gear 136 to the second gear 138 may be 1:2.3. A central shaft 137 of the second gear 138 is in mechanical communication with a rotor 140, and the rotor 140 rotates at the same speed as the second gear 138.

The rotor 140 includes an eccentric projection 142 formed away from an extension line of the central shaft 137 of the second gear 138. The eccentric projection 142 is accommodated in the cam 145. A groove (not shown) formed in a predetermined pattern so as to accommodate the eccentric projection 142 is formed in a surface of the cam 145, facing the eccentric projection 142. The groove is designed to interfere with movement in the X-axis direction of the eccentric projection 142, but designed not to interfere with movement in a Z-axis direction perpendicular to an XY plane. Accordingly, when the eccentric projection 142 rotates along a circle orbit inside the groove of the cam 145 with respect to the central shaft 137 of a Y-axis direction, the cam 145 reciprocates in the X-axis direction in conjunction with the movement of the eccentric projection 142 in the X-axis direction.

The piston 149 is coupled to an end portion of the cam 145 by virtue of which the reciprocating motion in the X-axis direction of the cam 145 compresses air while reciprocating in the X-axis direction. In one embodiment, the piston 149 is in mechanical communication with the end portion of the cam 145. The compressed air enters an injecting path 152. The injecting path 152 allows the compressed air to move toward the inside of the coupling block 120 (FIG. 1) and toward the inner space 114 (FIG. 5A) of the bellows-type airbag 112 (FIG. 5A). An outlet hole 153, which enables airflow into the coupling block 120, is formed in an end portion of the injecting path 152. The driving block 130 further includes a countercurrent preventing valve 156 for preventing a countercurrent of air from flowing back along the injecting path 152 towards the cylinder 147.

The driving block 130 further includes a discharging path 154 that branches off from the injecting path 152 and a decompression valve 158 formed at an end portion of the discharging path 154. The decompression valve 158 optionally induces the compressed air to flow toward the discharging path 154. In other words, when pressurization pressure of the radial artery 10 (see FIG. 1) is increased by expanding the inner space 114 (see FIG. 5A) of the bellows-type airbag 112, the decompression valve 158 closes the end portion of the discharging path 154. Also, when pressurization pressure of the radial artery 10 is decreased, the decompression valve 158 opens the end portion of the discharging path 154. Thus, air is discharged from the inner space 114 of the bellows-type airbag 112 to the discharging path 154, thereby decreasing pressurization pressure of the bellows-type airbag 112.

The motor 132, the deceleration unit 135, the cam 145, the cylinder 147, the countercurrent preventing valve 156, the injecting path 152, and the decompression valve 158 are all disposed on the same plane as the plane of the driving block 130 to make the driving block 130 slimmer. Since an extension line (parallel to the Y-axis) of the rotation shaft 133 of the motor 132 is at right angles to reciprocating motion directions (X-axis direction) of the cam 145 and the piston 149, the driving block 130 may be formed to be a more compact size.

Referring to FIG. 4, the result of operation of the pressurizing module 110 (see FIG. 1) disclosed herein is represented by curve (i), and the result of operation of a conventional pressurizing module is represented by curve (ii). Accordingly, for a pressurization pressure range (CA) of about 0 to 220 millimeters of mercury ("mm Hg") that is the blood pressure range of a human, the curve (i) has a gentle gradient of pressurization pressure to input voltage as compared to the curve (ii), thus precision control of pressurization pressure can be facilitated. Namely, in the case of the curve (i), variation in pressurization pressure of the bellows-type airbag 112 (see FIG. 1) according to the size of the input voltage that is input to the motor 132 (see FIG. 2) is small. Accordingly, when systolic blood pressure and diastolic blood pressure are measured using an oscillometric method, sphygmus wave data that is more suitable for the measurement of the blood pressure can be obtained by reducing the speed of pressurizing or decompressing the radial artery 10 (see FIG. 1). The pressurization pressure having a gently increasing gradient is caused by the deceleration unit 135 described with reference to FIG. 2 and depicted in the FIG. 2.

Referring to FIG. 3, the coupling block 120 includes a buffer chamber 126, a first hole 122 in fluid communication with the buffer chamber 126 and in fluid communication with the outlet hole 153 (see FIG. 2) of the injecting path 152 (see FIG. 2) so as to enable airflow. The coupling block 120 also includes a second hole 124 in fluid communication with the buffer chamber 126 and in fluid communication with the inner space 114 (see FIG. 5A) of the bellows-type airbag 112 so as to enable airflow. The first hole 122, the buffer chamber 126, and the second hole 124 are in fluid communication with one another so as to form a connection path that induces the compressed air discharged from the driving block 130 (see FIG. 2) to flow to the inner space 114 of the bellows-type airbag 112. The first hole 122 is formed in a location aligned with respect to the outlet hole 153 of the injecting path 152, and the second hole 124 is formed in a central portion of the coupling block 120 so as not to overlap the wrinkles 113 (see FIG. 5A) of the airbag 112. The buffer chamber 126 is designed so that fast inflow of the compressed air from the driving block 130 (see FIG. 2) does not cause a fast increase in pressurization pressure of the airbag 112. In other words, even if the compressed air quickly flows into the buffer chamber 126 through the first hole 122, the buffer chamber 126 has a volume that is large enough to accommodate a great deal of the incoming air that is introduced in a short period of time. Therefore, a fast inflow of air into the airbag 112 and the inner space 114 (see FIG. 5A) through the second hole 124 can be suppressed.

Referring to FIG. 5A, even if air flows into the inner space 114 of the bellows-type airbag 112 to expand the airbag 112, the curvature of the pressurizing surface 115 is not changed very much. This means that most of the pressurizing surface 115 corresponds to a valid pressurization area S1 that can pressurize a skin outside the radial artery 10 (see FIG. 1) at constant pressure.

A pouch type airbag 50 is formed by using flexible films 51 and 52 that face each other. The edges of the flexible films 51 and 52 are bonded to each other, as illustrated in FIG. 5B. When air flows into the inner space of the bonding portion 54 and the airbag 50 is expanded, the curvatures of the pair of films 51 and 52 become greater than the curvature of the pressurizing surface 115 (see FIG. 5A) due to an insufficient elasticity of the bonding portion 54. When a body part for which the blood pressure is measured is pressurized using the pouch type airbag 50, a valid pressurization area S2 can be pressurized at constant pressure and may be reduced in size. Thus, the possibility of success in measuring the blood pressure may be increased.

While aspects of the present invention have been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Thus, although a few embodiments have been shown and described, it would be appreciated by those of ordinary skill in the art that changes may be made to these embodiments without departing from the principles and spirit of the invention, the scope of which is defined in the claims and their equivalents.

What is claimed is:
1. A pressurizing module comprising:
a driving block for discharging compressed air; and
a bellows-type airbag formed to overlap the driving block; wherein the bellows type airbag is adapted to lie in a direction between the driving block and a body part where blood pressure is being evaluated; the bellows-type airbag comprising an inner space for accommodating the compressed air discharged from the driving block; a plurality of wrinkles flattened so as to expand the inner space, the plurality of wrinkles being disposed around the inner space; and a pressurizing surface formed at an end portion of the wrinkles and spaced apart from the driving block as the inner space expands;
wherein the driving block comprises a motor having a rotation shaft, a cam for converting rotary motion of the rotation shaft into a reciprocating motion in a direction perpendicular to an extension direction of the rotation shaft, a cylinder having a piston which is connected to the cam, where the piston reciprocates within the cylinder; and an injecting path formed between the cylinder and the bellows-type airbag so that the compressed air generated by the reciprocating motion of the piston moves toward the bellows-type airbag,
wherein the motor, the cam, the cylinder and the injecting path are disposed on the same plane as the plane of the driving block that is parallel to the extension direction of the rotation shaft and the reciprocation motion direction of the cam and is perpendicular to the direction between the driving block and the bellows-type airbag; and
a coupling block having a connection path to the bellows-type airbag; the coupling block being interposed between the driving block and the bellows-type airbag and induces the compressed air discharged from the driving block to flow into the inner space of the bellows-type airbag; wherein the coupling block comprises a buffer chamber inside the coupling block in order to suppress a fast inflow of air into the inner space of the bellows-type airbag.

2. The pressurizing module of claim 1, wherein the driving block further comprises a discharging path that branches off the injecting path, and a decompression valve formed at an end portion of the discharging path.

3. The pressurizing module of claim 1, wherein the coupling block comprises a hole; the hole allowing airflow between the connection path and the inner space of the bellows-type airbag; the hole being disposed in a manner so as not to overlap the wrinkles.

4. The pressurizing module of claim 1, wherein the driving block further comprises a countercurrent preventing valve for preventing a countercurrent of air from flowing along the injecting path to the cylinder.

5. The pressurizing module of claim 4, wherein the driving block further comprises a deceleration unit that is operative to transfer a rotation speed of the rotation shaft to a cam and is further operative to reduce the rotation speed of the cam relative to the rotation speed of the rotation shaft.

6. The pressurizing module of claim 5, wherein the deceleration unit comprises a first gear coupled to the rotation shaft and rotating at the same speed as the rotation shaft, and a second gear engaged with the first gear; the second gear having a diameter greater than that of the first gear.

7. The pressurizing module of claim 5, wherein the deceleration unit produces a gently increasing gradient in pressurization pressure in the pressurizing module of from about 0 mmHg to about 220 mmHg as the input voltage is changed from 0.4 volt to 1.9 volt.

8. A blood pressure measuring device for pressurizing a blood vessel of a patient, the blood pressure measuring device comprising:
- a pressure sensor attached to a pressurizing surface of the bellows-type airbag and detecting a sphygmus wave and pressure of a blood vessel from the blood vessel;
- a blood pressure calculation processor calculating blood pressure of the patient on the basis of the sphygmus wave and the pressure of the blood vessel detected in the pressure sensor; and
- a pressurizing module comprising:
- a driving block for discharging compressed air; wherein the driving block comprises a motor having a rotation shaft, a cam for converting rotary motion of the rotation shaft into a reciprocating motion in a direction perpendicular to an extension direction of the rotation shaft, a cylinder having a piston which is connected to the cam and where the piston reciprocates within the cylinder, and an injecting path formed between the cylinder and the bellows-type airbag so that the compressed air generated by the reciprocating motion of the piston moves toward the bellows-type airbag; and

- a bellows-type airbag formed to overlap the driving block; wherein the bellows type airbag is adapted to lie in a direction between the driving block and a body part where blood pressure is being evaluated; the bellows-type airbag comprising an inner space for accommodating the compressed air discharged from the driving block; a plurality of wrinkles flattened so as to expand the inner space, the plurality of wrinkles being disposed around the inner space; and a pressurizing surface formed at an end portion of the wrinkles and spaced apart from the driving block as the inner space expands, wherein the motor, the cam, the cylinder and the injecting path are disposed on the same plane as the plane of the driving block that is parallel to the extension direction of the rotation shaft and the reciprocation motion direction of the cam and is perpendicular to the direction between the driving block and the bellows-type airbag; and a coupling block having a connection path to the bellows-type airbag; the coupling block being interposed between the driving block and the bellows-type airbag and induces the compressed air discharged from the driving block to flow into the inner space of the bellows-type airbag; wherein the coupling block comprises a buffer chamber inside the coupling block in order to suppress a fast inflow of air into the inner space of the bellows-type airbag.

9. The blood pressure measuring device of claim 8, wherein the blood vessel is a radial artery inside a patient's wrist.

10. The blood pressure measuring device of claim 9, further comprising a wrist band adapted to surround the patient's wrist so as to attach the blood pressure measuring device to the patient's wrist.

* * * * *